(12) United States Patent
Le Pesant et al.

(10) Patent No.: US 6,712,287 B1
(45) Date of Patent: Mar. 30, 2004

(54) PROGRAMMABLE DEVICE FOR DIFFUSING OLFACTORY PEAKS

(75) Inventors: Jean-Pierre Le Pesant, Ventabren (FR); Jean-Claude Millet, Bourg les Valence (FR)

(73) Assignee: Osmooze S.A., Bourg les Valence (FR)

( * ) Notice: Subject to any disclaimer, the term of this patent is extended or adjusted under 35 U.S.C. 154(b) by 0 days.

(21) Appl. No.: 09/926,809

(22) PCT Filed: Jun. 22, 2000

(86) PCT No.: PCT/FR00/01745

§ 371 (c)(1),
(2), (4) Date: Jul. 15, 2002

(87) PCT Pub. No.: WO00/78467

PCT Pub. Date: Dec. 28, 2000

(30) Foreign Application Priority Data

Jun. 22, 1999 (FR) .......................................... 99 07939

(51) Int. Cl.[7] .............................................. A01G 27/00
(52) U.S. Cl. ........................ 239/67; 239/69; 239/346; 239/369; 239/426; 261/26
(58) Field of Search ............... 239/67, 69, 70, 239/102.2, 326, 340, 346, 369, 433, 426, 434; 261/26

(56) References Cited

U.S. PATENT DOCUMENTS

| | | | | |
|---|---|---|---|---|
| 4,702,418 A | * | 10/1987 | Carter et al. .............. 239/101 |
| 5,038,972 A | * | 8/1991 | Muderlak et al. ............ 222/25 |
| 5,060,864 A | * | 10/1991 | Nishi et al. ................ 239/289 |
| 5,154,893 A | | 10/1992 | Nakade |
| 5,248,087 A | * | 9/1993 | Dressler .................. 239/102.2 |
| 5,370,829 A | | 12/1994 | Kunze |
| 5,452,362 A | * | 9/1995 | Burward-Hoy ............. 381/71.5 |
| 5,485,828 A | | 1/1996 | Hauser |
| 5,487,502 A | * | 1/1996 | Liao ............................ 239/69 |
| 5,591,409 A | | 1/1997 | Watkins |
| 5,724,256 A | * | 3/1998 | Lee et al. ................... 700/285 |
| 5,727,732 A | * | 3/1998 | Stein ............................. 239/1 |
| 5,781,640 A | * | 7/1998 | Nicolino, Jr. .............. 381/73.1 |
| 5,887,118 A | | 3/1999 | Huffman et al. |
| 6,066,791 A | * | 5/2000 | Renard et al. ............ 84/477 R |
| 6,267,297 B1 | * | 7/2001 | Contadini et al. ............ 239/1 |
| 6,279,836 B1 | * | 8/2001 | Toetschinger et al. ........ 239/70 |
| 6,293,474 B1 | * | 9/2001 | Helf et al. ................ 239/102.2 |
| 6,371,451 B1 | * | 4/2002 | Choi ........................... 261/26 |
| 6,422,303 B1 | * | 7/2002 | Ishida et al. ................ 165/80.3 |
| 6,502,762 B2 | * | 1/2003 | Tuttobene, Jr. .............. 239/59 |
| 6,536,746 B2 | * | 3/2003 | Watkins ....................... 261/26 |
| 6,581,915 B2 | * | 6/2003 | Bartsch et al. ................ 261/26 |

FOREIGN PATENT DOCUMENTS

| | | | |
|---|---|---|---|
| WO | 98/39687 | 9/1998 | |
| WO | WO 99/38102 | * 7/1999 | ............ G06G/7/48 |
| WO | 00/12143 | 3/2000 | |

* cited by examiner

Primary Examiner—Henry Bennett
Assistant Examiner—Amanda Flynn
(74) Attorney, Agent, or Firm—Dennison, Schultz, Dougherty & MacDonald (57) ABSTRACT

A programmable odor-bearing substance diffusion device includes a number n of odor diffusion devices, where n is equal to or greater than 1, each odor diffusion device including a store of an odor source which is dispensed by the odor diffusion device, a device for independently controlling each odor diffusion device to emit a single odor or a mixture of odors from a by a combination of p of the n stores, and a programmable control device for establishing odor peak emission cycles and a predetermined interval between two successive emission cycles, the predetermined interval being based on an olfactory saturation and desaturation times of the olfactory system of a user.

27 Claims, 4 Drawing Sheets

PROGRAMMABLE DEVICE FOR DIFFUSING OLFACTORY PEAKS

FIELD OF THE INVENTION

This invention concerns a programmable device for the diffusion of active substances, such as odour-bearing products, intended among other things, to produce olfactory sensations or messages for educational, practical or play-related purposes.

In a prior embodiment, there is industrial or personal equipment for the diffusion of odour-bearing products (perfumes, deodorants) or sanitary products (insecticides, bactericides). They are capable of diffusing these products by a spray, either at regular intervals or in response to a detected action, such as the opening of a door or the detection of presence.

DESCRIPTION OF RELATE ART

Accordingly, through the request for European patent EP-A-0714 709, there is a known device for the projection of drops on request. This document describes a device which includes one or several sets of nozzles connected to one or several tanks containing the product to be diffused. An electronic control device is capable of diffusing, as chosen, one or several products, independently or in sequence. The diffusion can be triggered by a proximity detector or by a programmable timer system.

Most of the devices that now exist using means of nebulisation by an air jet bearing a single odour, without programming, or at least, with very basic emission cycles, as described in the document EP-A-0714 709. The devices are unsuitable for the physiology of the users, in particular because they do not take into consideration the saturation of the olfactory nerve endings and the ambient habituation effect. Other known devices obtain odour diffusion by the control of an air flow over a surface containing the olfactory principle to be evaporated. These devices have the same drawbacks as the former.

In addition, these devices are particularly restricted in terms of multiple and combinational use of odours

SUMMARY OF THE INVENTION

Accordingly, the purpose of the invention is a programmable odour distribution device having carefully designed operating characteristics to allow for the physiology of the user.

In particular, devices according to the invention will be capable of generating odour peaks by taking into consideration the physiological characteristics of the users.

For this purpose, the invention proposes a programmable device for the diffusion of odour-bearing substances comprising a number n of odour diffusion means where n is equal to or greater than 1, each of which can be controlled independently to emit, from appropriate reserves, odours or mixtures of odours by the combination p of n sources. According to the invention, the device also includes programmable control means capable of establishing odour peak emission cycles having determined emission times and determine intervals between two successive emissions which successive emission cycles of odour peaks take into consideration the saturation and desaturation times of the user olfactory systems.

It should be understood that this saturation effect is caused by a neuro-sensory inhibition of signals emanating from olfactory capture cells, beyond a determined period of exposure to the same odour. The purpose of the invention is therefore to emit odour peaks according to the transmission times and the intervals between two successive emissions taking into consideration the physiological characteristics of the user olfactory systems, that is, the saturation effect of these olfactory systems. Indeed, after some exposure to the same odour, signals from the olfactory capture cells are no longer acknowledged by the brain so that the odour is no longer perceived by the user. A change in the user odour-bearing environment, obtained by the emission of another odour peak, will permit further perception of the odour by the user, through to the effect of saturation of the olfactory system.

The purpose of the invention involves renewing cyclically the olfactory perception of the users by taking their neuro-sensory characteristics into consideration. The diffusion of odour-bearing substances as odour peaks leads to decreasing the quantity of odour-bearing substances diffused, compared to permanent diffusion. Accordingly, diffusion as odour peaks avoids phenomena of olfactory habituation, causing for instance, headaches or a nauseous feeling, occurring during the permanent emission of odour bearing substances.

For information, odour peaks have typical emission times of between five seconds and two minutes, and intervals between typical emissions of two minutes to one hour and, preferably, between two and 15 minutes.

Preferably, the odour peaks have typical emission times of 15 seconds to one minute and, preferably,of around 30 seconds and intervals between typical emissions of between two minutes and five minutes.

Devices like this can generate odour peaks for people spread out in such places as an office, a meeting room, a lounge, a bedroom etc.

Depending on the various optional engineering methods, this invention is capable of incorporating one or several of the following aspects, depending on the choices of use and the applications envisaged:

- a number n of active principle diffusion means equal to or greater than 2.
- vaporisation means consisting of diffusion means suitable for the emission of drops sized in such a way as to produce a dry fog effect, with the elementary diameter of a drop of being in the region of 0.5 to 3 microns;
- vaporisation means consisting of surface evaporation means such as a flow of air;
- active means of attenuating or eliminating noise in the form of noise abatement means;
- passive means of noise attenuation;
- means of diffusing drops operating by Venturi effect;
- means of diffusing drops including an electro-mechanical activating device, for instance, a piezo-electric actuator, arranged so as to transmit vibrations toward a load of liquid and eject droplets from this load of liquid;
- means of diffusing drops which include means of producing a jet of liquid to be diffused and means of generating acoustic surface waves on the jet of liquid so as to detach droplets from this jet;
- programmable control means which include signal input means intended to be connected to at least one physiological parameter sensor designed to control the activation and/or evolution of a program for the diffusion of active parameters depending on one or several detected physiological parameters; a physiological parameter sensor in the form of a device detecting the noise caused by snoring, with the device programmed to control the means of diffusion and trigger the emission of odour bearing product(s) in order to cause the snoring to stop;

a physiological parameter sensor consisting of a drowsiness detector with the device programmed to control the means of diffusion and trigger the emission of odour bearing product(s) depending on the detected physiological state;

a detector of the electrical characteristic of the user organism, for instance electrical activity or resistivity detected by electrodes;

programmable control means including means of counting time so as to control the activation and/or evolution of an odour diffusion programme or of other active principles according to one or several time-related parameters;

the programmable control means can be programmed to begin, and a set time, the diffusion cycle apt to awaken the subject;

the programmable control means can be programmed to begin, at a programmed time or in response to an input at one of the interfaces, a diffusion cycle apt to accompany the act of falling asleep;

the programmable control means include audio output means capable of managing the emission of sounds to accompany a diffusion programme;

one at the start the various tanks of the diffusion means contains an odour-bearing liquid specific to this tank, for instance, an essential oil;

a preparation used as a means of soliciting an awakened state from the comatose state of a patient with at least one of the tanks containing an odour bearing liquid chosen to emit an odour redolent of the past or surroundings or tastes of the patient;

at least one of the liquids contains a pheromone related to the filiation of the patient;

The odour peak generating cycles are calculated to take into consideration the saturation and de-saturation time of the olfactory nervous system while adding a waiting period to give the user time to create his desire for the odour peak and thus reinforce his pleasure when it arrives;

the device also includes automatic means of recognising the product contained in a tank by a predetermined coding system with respect to the recipient containing the liquid, and adjusting the diffusion programme accordingly;

the electric power supply can be obtained by connecting the system to the electric circuit of a real call, for instance the cigarette lighter in the vehicle;

the device is a portable system allowing personal and individual use;

the device includes audio means associated with the odour diffusion systems capable of sending out a global and consistent odour-sound message related to nature.

For operation to be beneficial in some applications, the means of diffusing the drops will preferably be of the more or less silent type.

The device may incorporate active means of attenuating or eliminating noise consisting of antinoise means and/or passive noise attenuation means.

The means of forming the drops can use a variety of techniques, for instance:

means working by a Venturi effect which means may include at least one liquid outlet to having a first end designed to be immersed in the tank of liquid to be diffused and a second end designed to be exposed to a flow of air, which second end has a smaller section. The flow of air comes from a tube converging at one end to ensure the high speed outlet of air near the mouth of the liquid outlet tube which liquid outlet tube and air outlet tube could advantageously have a diameter of between 0.05 and 2 mm, and preferably, between 0.2 and 1 mm;

means operating by an electromechanical actuator, for instance, a piezoelectric actuator arranged to transmit vibration toward a load of liquid and eject the droplets from this load of liquid. In this case, the load of liquid may be contained in a cavity which has on its plane parallel faces, respectively, ejection orifices and the actuator. In this mode, the actuator is preferably supplied by excitation voltage at high frequency, generating acoustic vibration beyond the audible spectrum, or otherwise means operating on the basis of acoustic surface waves comprising means of producing the jet of liquid to be diffused and means of generating acoustic surface waves on the jet of liquid so as to detach droplets from the jet.

In an advantageous embodiment, the means of programming the diffusion of drops will include means of input for the signal to be connected at least one physiological parameter sensor capable of controlling the activation and/or evolution of a drop diffusion program depending on one or several detected physiological parameters.

The means of diffusion may be of the semi-passive type, i.e. based on the evaporation of the liquid containing the odour-bearing active principle by the programmed passage of a flow of air. Throughout this text, the term "odour-bearing" will be understood to cover the action of generating awareness of the sense of smell related to the olfactory nerve endings and the result of soliciting the vomeronasal organ by pheromones bearing specific olfactory messages.

In this case of semi-passive diffusion means, the means of forming a flow of air with the means of stocking an odour-bearing liquid, gel or solid in a cartridge will be associated to offer a large surface for evaporation. In this case, the device will advantageously be operated in the immediate surroundings of the user, for instance at between 1 and 2 meters. If a fog is diffused, as in the case of evaporation, the goal is still the same, obtaining odour peaks.

For instance, the device could be associated with a physiological parameter sensor such as a noise detector triggered by snoring with the device programmed to control means of odour diffusion so as to cause the emission of the odour-bearing product(s) in response to detected snoring so as to eliminate the snoring by the inhalation of this odour-bearing product, itself formulated in such a way that it works on the breathing organs of the snoring person.

In another example, the device could also be associated with a physiological parameter sensor consisting of a drowsiness state detector, with this device programmed to control means of odour diffusion and provoke the transmission of products according to the detected physiological state. As an example, the physiological parameter sensor could include at least one of the following:

a respiration detector, and an electric characteristic detector on the user's organism, for instance, electrical activity or resistivity detected by electrodes, for instance in terms of cerebral activity.

In the various configurations of the aforementioned device, the diffusion programming means to generate an odour peak may also include time counting means capable of controlling the activation and/or evolution of an odour diffusion program according to one or several time-related parameters.

In one particular application of the invention, the means of programming the diffusion of odour peaks could be programmed to begin, at a programmed time, a diffusion cycle of drops that could cause awakening.

Odour diffusion programming means could also be programmed to begin at a programmed time, or in response to an input into one of the interfaces, an odour peak diffusion cycle which could assist with drowsiness.

In several advantageous modes of this invention, the odour peak diffusion programming means could include audio output means to generate the emission of sounds to accompany an odour peak diffusion program.

For many applications, at least one of the various tanks containing the diffusion means would be provided with a liquid (or gel or solid) of the odour-bearing type specific to the tank, for instance an essential oil. However, other products could be considered: active principles, sanitary products, etc.

In a given embodiment, the device could be prepared to solicit awakening from a comatose state in a patient, with at least one of the tanks containing the odour-bearing liquid chosen to emit an odour related to the physiological or affective activity of the patient (relation with parents, spouse, loved ones).

At least one of these liquids may contain pheromones related to the filiation or environment of the patient.

BRIEF DESCRIPTION OF THE DRAWINGS

Better understanding of the invention will be obtained, with its particular advantages, from reading the description of the preferred embodiments of the invention, given purely as non-limitative examples with reference to the attached illustrations in which.

DESCRIPTION OF THE PREFERRED EMBODIMENTS

Figure 1:
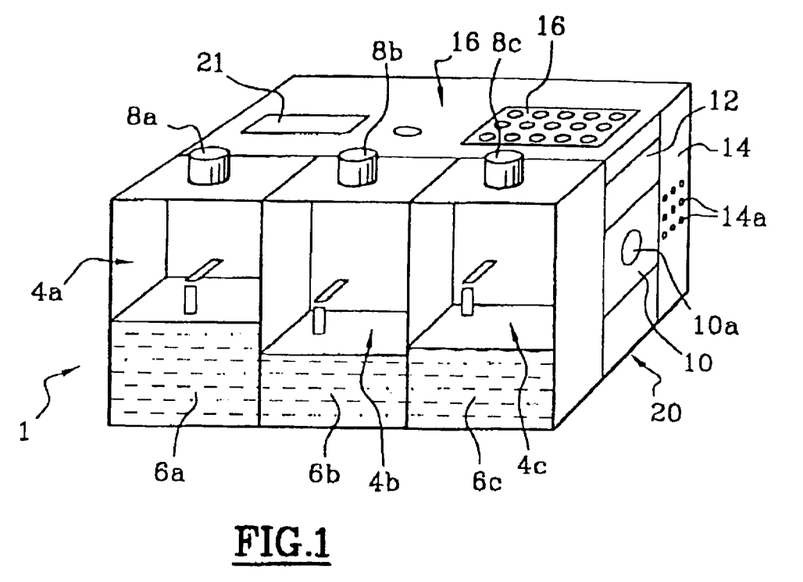
FIG. 1 is a general schematic view of a programmable vaporization device in conformity with this invention.

FIG. 1 is a schematic view of all the assembled parts forming the programmable product diffusion device according to an initial embodiment of the invention.

Figure 2:
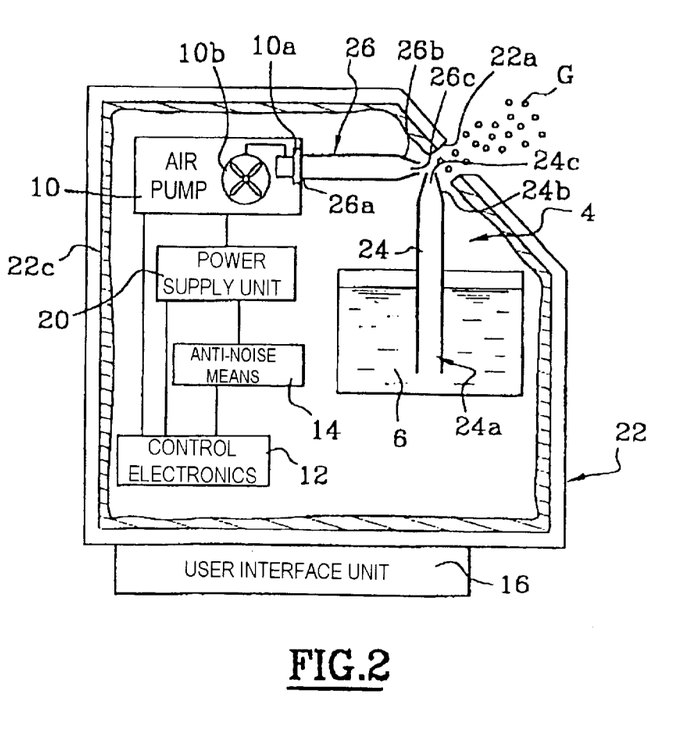
FIG. 2 is a schematic diagram of a means of drop diffusion according to an initial embodiment of the invention.

Device 1 is a box structure containing, in a functional whole, all the following components or subassemblies:

- droplet emission means, comprising, in the example a number n of three nebulization units 4*a*, 4*b* and 4*c*, each forming drop diffusion means. Each nebulization unit is linked with a tank of product to be diffused, specific to it, 6*a*, 6*b*, 6*c* and also includes its own outlet of nebulized droplets into the atmosphere 8*a*, 8*b* and 8*c*. The tanks may be extractable and interchangeable;
- an air flow generator comprising one or several air pumps 10, designed to supply nebulization units 4*a*, 4*b* and 4*c* to ensure their operation from an air inlet 10*a;*
- an active anti-noise generator 142 including an acoustic energy output 142*a* designed to eliminate, or at least attenuate, the sound emissions of the device, in particular those emanating from the air flow generator 10, by a destructive interference phenomenon;
- control electronics 12 including a programming unit and used more particularly to control the salvos of drops selectively from nebulization units 4*a*, 4*b* and 4*c;*
- an interface unit having a programming data input keyboard 16 and a display device 21 to indicate the operating state of the device, and an electric power supply unit 20 supplying the voltages needed by the various parts of device 1 from an internal battery or a mains connector. It will be possible to add to these means, either by integration in the same package, or by connection, one or several of the following means:
  - means of creating a sound environment (music, voice, sound effects, etc.) from a recorded medium (compact disk, cassette) or a sound synthesizer and
  - means of detection and triggering making it possible to activate and modify various functions programmed according to the detected parameters (elapsed time, physiological parameters, ambient brightness, ambient noises, presence of people, etc.).

To permit the implementation of device 1 according to certain applications, in particular those related to awakening and/or falling asleep, one of the parameters may be related to the physiological activity of a person: breathing rate, cardiac rate, sound emission, such as snoring, electrical activity of the nervous system (electroencephalogram or others), etc. In this case, the control electronics will have a sensor input for one or several of the parameters mentioned at a suitable interface (cf. FIG. 7). Depending on the data supplied by these sensors, the control electronics will be capable of tripping or changing a program to activate the drop diffusion means 4.

Anti-noise means 14 can be an advantage in some applications, in particular those related to falling asleep or waking up, if the organs of the device tend to emit a sound level considered to be too high into the environment.

These anti-noise means 14 could replace or complement passive noise attenuation means such as phonic absorption surface coatings.

Accordingly, the base of the device consists of drop emission means 4 which, to a given program, make it possible to generate very fine droplets, highly monodispersed, of a liquid. This could be a liquid containing an odour-bearing principle, which might preferably be a natural plant extraction, referred to as essential oils.

As appears below in the description, these multiple means of drop diffusion 4 can work in series or in parallel from tanks 6 containing liquids with different odour-bearing properties, as mentioned above.

The means of drop emission (referred to generically by reference 4) can be based on a variety of techniques, of which three examples, corresponding to respective engineering modes, are now described as an example.

According to the following engineering modes, the implementation of some of the devices described in FIG. 1 may be pointless or optional. The professional will easily understand the necessary adaptations to take this into consideration.

FIG. 2 is a schematic view of a drop emission means 4 G, conforming to an initial embodiment, functionally integrated into the devices of FIG. 1, housed in a case 22. Naturally, case 22 includes several of these drop emission devices 4, each controlled independently.

The means of drop emission 4 includes a first and second tube 24 and 26 respectively connected to a tank containing the liquid to be diffused 6, for instance in the form of an interchange cartridge and an air pump outlet 10.

The first tube 24 has its first end 24a immersed in liquid tank 6, and second end 24b having a conical section converging toward a smaller section outlet 24c. This conical flared shape at second end 24b of the first liquid inlet tube is advantageous because it facilitates the forming of drops by pulling them away from the surface of the liquid meniscus at this end 24b.

The second tube 26 has a first end 26a connected to air outlet 10a of air pump 10 and a second end 26b also having a tapered section converging on a smaller section mouth 26c.

The first and second tubes 24 and 26 are arranged at right angles, the first here being vertical with the ends at mouths 24c and 26c of the two tubes near one another.

In operation, a jet of air from mouth 26c of second tube 26 passes over mouth 24c of first tube 24.

With this arrangement, the jet of air, by a Venturi effect, draws the liquid into the first tube and projects it in fine droplets G, carried by the jet of air.

In an advantageous embodiment, these means of pulverization by Venturi effect 24 and 26 will be constructed with small size and weight to permit a suitable capability of projection for uses related to waking up, and to other applications of the device described below.

As an example, the first and seconds tubes 24 and 26 used in this engineering method have a diameter of around 0.2 to 1 millimeter.

The outlet of the droplets G is through an opening 22a specially provided in case 22, and which can be provided with means of recirculation for the larger drops, to prevent them being carried off into the atmosphere.

Air pump 10 controls the flow of droplets G by means of the emitted air flow, and the flow rate depends on the speed and intensity of this flow. Accordingly, pump 10 is controlled by control electronics 12 to supply a variable flow of air in second tube 26, according to established programming chosen by the user at interface 16, or to a pre-established program. In the example, air pump 10 includes a single tubing 10b feeding each of several air flow outlets 10a which supply respective tubes 26 of the various drop-emitting means 4 of the device. In this case, the air flow is controlled by means of flow testing devices, for instance solenoids, associated with each of outlets 10a. These means are controlled individually by control electronics 12.

The anti-noise device 14 is arranged and controlled to eliminate or attenuate the unwanted sound emissions of the device, which come essentially from the mechanicals of the air pump 10, in particular turbine 10b. Accordingly, the anti-noise device 14 is mounted near air pump 10.

It includes a sound emission sensor directed toward the mechanicals of the pump and means of producing at the acoustic energy output 14a the same sound emission, but with a sound wave phase-shift of 180°. The phase-shifted acoustic energy emission thus interferes destructively with the sound emission detected by the sensor (in this case coming from the pump mechanicals), so that it is eliminated or considerably decreased.

The principle of operation and engineering of the anti-noise devices designed to fulfil the envisioned application are well known to the professional and are not detailed here out of a concern for concision. The case 22 also includes coating 22c of noise-absorbing material on all its inside walls. This coating consists of a passive noise attenuation means, used here as a complement to anti-noise means 14. A similar noise attenuation coating may enclose air pump 10 in addition to or instead of coating 22c.

It is possible to have an individual air pump 10 for each drop emission means 4. Control electronics 12 then operate on each of air pumps 10.

It is then possible to provide for an associated anti-noise device 14, as explained previously, on each air pump, or to have a single anti-noise device 14 comprising sound detectors to detect the noise from the various pumps so that the acoustic emission represents a phase-shifted spectrum of the different captured noises.

The operating energy of air pump 10, anti-noise device 14, control electronics 12 and interface 16 is obtained by electric power supply 20.

Figure 3:
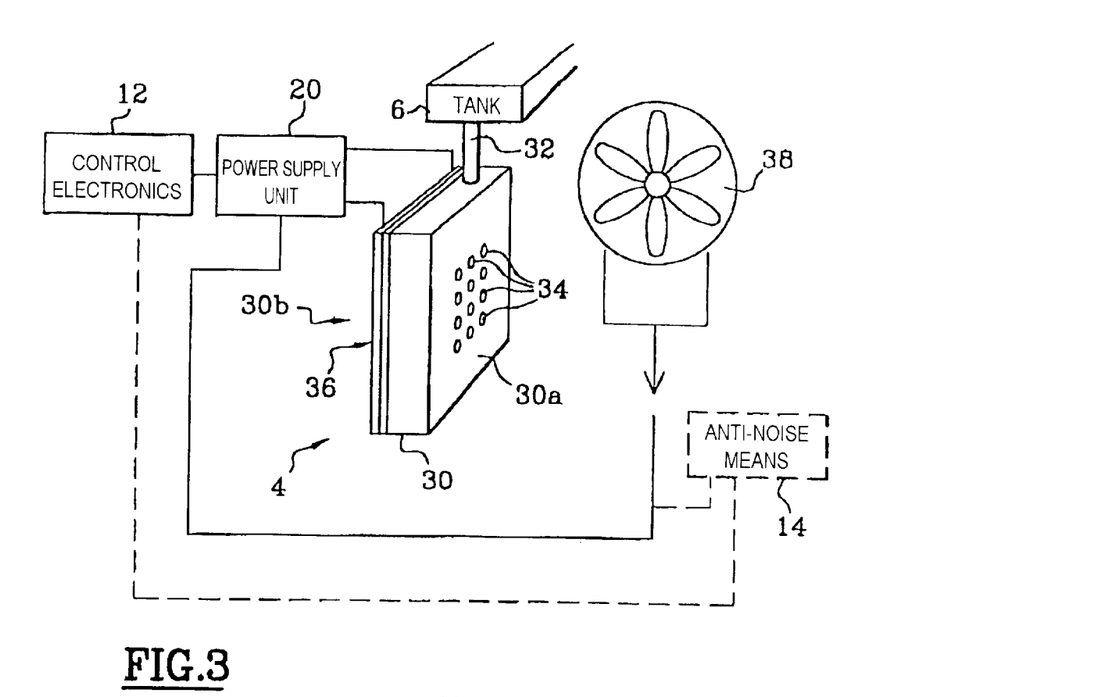
FIG. 3 is a schematic diagram of a drop diffusion means according to the second embodiment of the invention.

FIG. 3 illustrates a means of emitting droplets 4 operating on the basis of acoustic waves, according to a second embodiment of the invention.

This means comprises a cavity 30, forming a store of liquid, supplied with the liquid to be diffused by a supply tube 32 connected to a liquid tank 6.

Cavity 30 has a main first face and second face 30a and 30b that are approximately plane and parallel to one another. First face 30a consists of a plate pierced with holes passing through it, forming small diameter orifices 34, for instance 1 to 10 microns with typical values ranging from 2 to 6 microns, values given for information only.

Second face 30b has a piezoelectric actuator 36 electrically connected to electric power supply 20. It includes means forming a membrane taking up more or less the entire second face 30b of the cavity.

When the means forming the membrane receive an AC excitation voltage from the electric power supply 20, they transform the electric energy into vibrating mechanical energy according to the piezoelectric principle. This high frequency vibrating energy produces acoustic waves which, when transmitted into cavity 30, engender overpressure in the liquid contained within it. These high frequency overpressures provoke the expulsion of the liquid through orifices 34 of plate 30a in the form of fine droplets.

As a non-limitative example, the frequency of the piezoelectric actuator could advantageously be around 100 to 300 kilohertz, which frequencies are not audible to the human ear. The droplets formed in this way are then blown into the atmosphere by a weak jet of air, produced for instance by a small fan 38 connected to electric power supply 20. This fan can be integrated either into drop emission means 30 or into the assembly housing it.

As an alternative, piezoelectric actuator 36 can be replaced by an electrostatic or acoustic actuator.

The flow of drops or droplets can be adjusted by means of the AC excitation voltage of actuator 36 (piezoelectric or depending on chosen variants), such as: signal amplitude, current intensity, frequency and/or cyclic ratio of the waveform. These parameters can be controlled on power supply 20 from control electronics 12.

The integration into the programmable diffuser of a battery of drop emission means 4 according to the second embodiment, can be particularly compact. Fan 38 may be a single unit for the entire battery of drop emission means 4 or may be specific to each of these means, then controlled individually by control electronics 12.

This second embodiment is a particularly silent type because the frequency range of actuator 36 is not in the audible domain, and fan 38 can easily be made to operate silently. However, it is possible to add, as an option, an anti-noise device 14 (shown in dotted lines in FIG. 3), arranged in the same way as for the first embodiment.

Figure 4:
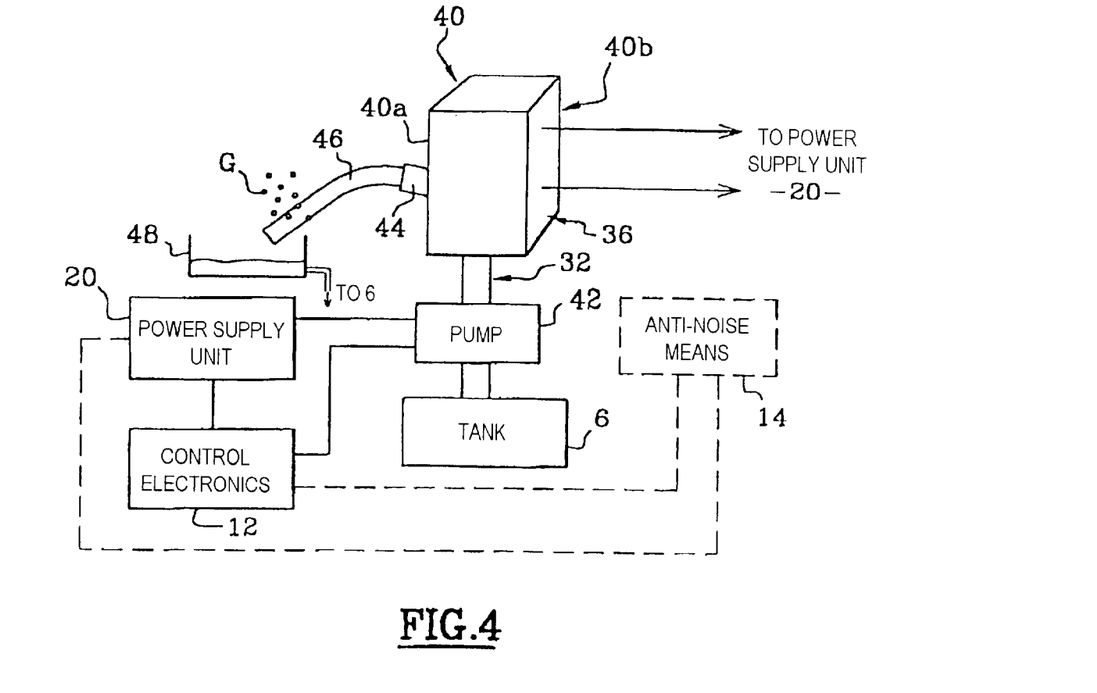
FIG. 4 is a schematic diagram of a drop diffusion means according to the third embodiment of the invention.

According to a third embodiment schematically shown in FIG. 4, the drop emission means 4 consist of a low power pump 42 and piezoelectric means forming droplets by creating, by piezoelectric resonance excitation, instabilities in the surface waves of liquid jet 46 produced by the pump or by the piezoelectric excitation itself.

These means include a box-shaped cavity 40 designed to contain provisionally the fill of liquid to be expelled in the form of droplets G. Cavity 40 is supplied with liquid by tube 32 connecting its inside to liquid tank 6 via low power pump 42.

Cavity 40 has a more or less parallel first face and second face 40a and 40b. First face 40a includes a nozzle (or possibly several) for liquid ejection 44, connecting the inside of cavity 40 to the outside. As will be explained below, liquid 46 is emitted by the nozzle or nozzles 44, in the form of a jet from which droplets G are created. The liquid from jet 46, not transformed into droplets, is recovered by plate 48 and returned to tank 6.

The second face 40b includes a piezoelectric power actuator 36 connected to electric power supply 20. Its operating mode is similar to that of the second embodiment, in particular concerning the control of the excitation voltage, and will not be repeated for the sake of concision.

In operation, pump 42 supplies cavity 40 with liquid from a jet of liquid 46 via the nozzle(s) 44.

In response to an excitation voltage applied to actuator 36 by electric power supply 20, the latter produces acoustic surface waves at the jet of liquid 46. These surface waves are coupled with the capillary surface waves of jet 46 provoking surface instabilities in it. Excitation on resonance of these instabilities causes increasing amplitude asperities to form, resulting in the asperities being detached in the form of droplets G with size depending on excitation conditions and viscosity and surface tension characteristics of the liquid used.

Accordingly, it is possible to control the characteristics of the droplets (size, density, velocity, etc.) by adjusting one or several parameters such as the force of the jet (determined by the nozzle(s) and the flow rate of pump 42), the characteristics of actuator 36 and/or the excitation voltage (frequency, amplitude, current, etc.).

The droplets G obtained in this way are diffused to the outside, if necessary using a fan (not shown). In an embodiment of this third method using a fan to disperse the droplets, the possibilities described for the second embodiment apply similarly in this mode and will not be repeated for the sake of concision.

In the same way as the second embodiment, this embodiment is of the silent type, and pump 42 can have a very low sound emission. Nevertheless, it is possible to add optionally to pump 42 (and/or to a fan if used) an anti-noise device 14 as described previously.

Further, note that passive noise attenuation means (for instance a coating like 22c) may be used for all the different methods available.

In all the described methods, the size of the emitted droplets will be set according to utilization criteria so as to ensure the correct operation of the droplet projecting device and to provide the user with satisfaction and comfort as needed. The droplet size will generally be small enough to permit rapid evaporation after projection into the atmosphere. This condition will, on the one hand, prevent liquid from running around the nebulizing apparatus, and will also provide for fast and consistent mixing with the ambient air.

An order of magnitude of the drop diameter will make it possible to fulfill these conditions, given for information only, as 1 to 2 microns. This drop size will obtain what is commonly referred to as a "dry fog". Means of diffusing very small droplets in high numbers like this are well suited to the volume of residential rooms and meeting rooms, typically containing air volumes of between 30 and 100 cubic meters.

Figure 5:
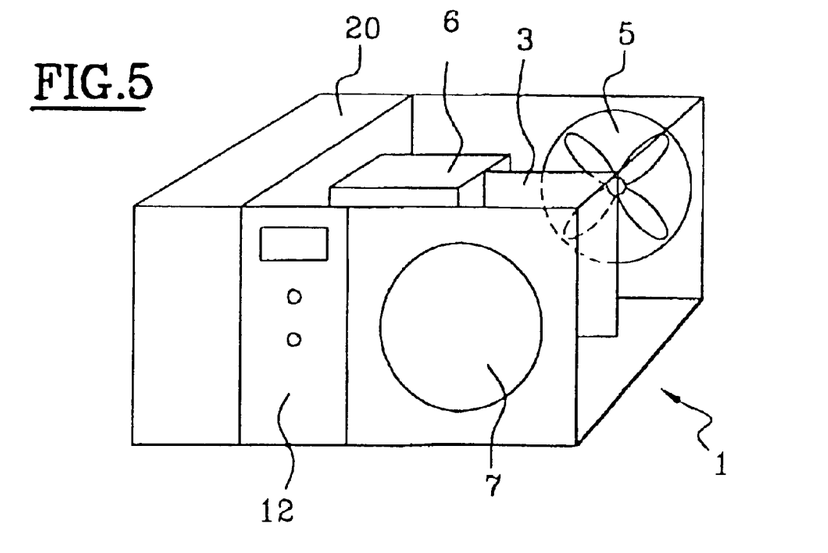
FIG. 5 is a schematic diagram of a vaporized liquid diffusion means by an air flow.

FIG. 5 is a schematic view of all the assembled elements forming the programmable product diffusion device in an embodiment of the invention which, contrary to the previous modes, does not involve the creation of drops to be evaporated but direct evaporation on the exposed surface of the liquid or gel or other material, comprising active principles, in particular odour-bearing principles.

In method shown in FIG. 5, a single diffusion element is indicated, but the professional will easily understand that this element may be duplicated n times, as already explained.

The device 1 contains in a box, an electric power supply 20 consisting of batteries or cells and/or, industry, means of connection to an external electric power supply, a user control interface 16 and active product diffusion means, for instance odour-bearing emission).

In this method, the active product diffusion means, or each of these means, include(s):

a diffusion substrate 3 connected to an active product tank 6, in such a way that the substrate is impregnated with the active product. This substrate 3 is porous and allows an airflow to pass through, obtained either by a very fine mesh, or by perforation;

a fan 5 placed upstream of the diffusion substrate 3 surface so as to direct a flow of air towards it; and a diffusion outlet 7 downstream of the diffusion substrate 3, designed to evacuate the flow of air from the fan after passing through the diffusion substrate.

It is possible to provide a fan 5 for each diffusion means, or a single fan ensuring the flow of air for a group, or for all the diffusion means considered together.

Depending on the size of the diffusing device and the volume of the airflow, the quantities of diffused product, as a non-limitative example, could be included between 0.01 et 1 microliter (millionth of a liter) per minute, for airflow is included between 0.5 and 5 cubic metres per hour and electric power values included between 02 and 2 watts.

Devices like this are well suited for effect in the immediate surroundings of the user, typically at a distance of between 1 and 2 m.

Figure 6:
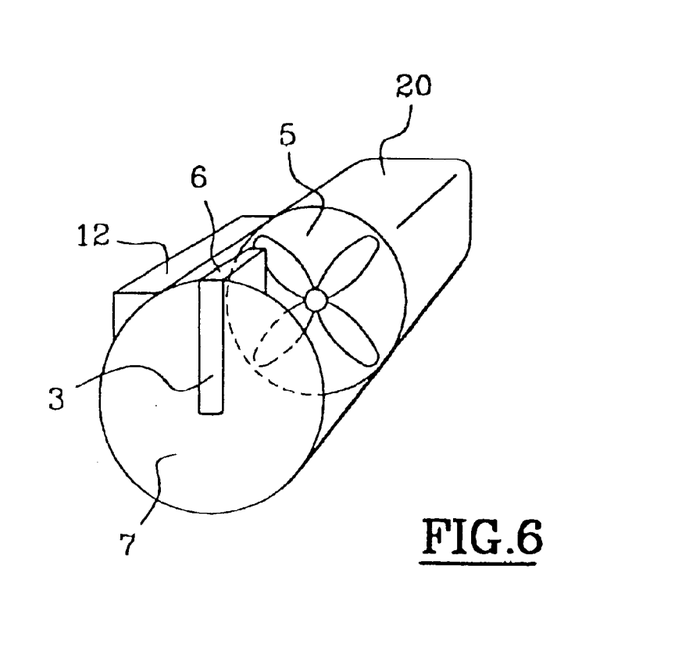
FIG. 6 is a schematic diagram of an alternate diffusion means for a liquid vaporized by an air flow.

The FIG. 6 is estimated view of a programmable product diffusion device according to an embodiment of the invention, more particularly intended for use in vehicles such as automobiles, trucks, coaches, etc.

Each element shown in this figure having a function similar to an element already described by reference to FIG. 5 bears the same reference number and will not be described again for the sake of concision. Note that diffusion substrate 3 in this case is more or less in the outlet plane 7 for diffusion into the atmosphere and that the configuration of all the components is substantially more compact because it is designed for onboard use.

In this embodiment, the electric energy is supplied by the vehicle electricity circuit, powered by the battery, for instance, through the vehicle cigarette lighter or any other electrical connection for accessories. The device schematised in FIG. 6 could advantageously include a timed electronic subassembly to detect the level of voltage supplied by the vehicle electricity system. In this way, when the vehicle is running, the voltage level is maintained essentially constant, with frequent fluctuations due to the activity of the engine and the accessories (indicator lights, windscreen wipers, headlights, etc) over intervals of time lasting several minutes. Conversely, when the vehicle is not running with the engine off, for instance for several minutes, the fluctuations will disappear and the timed electronic subassembly will stop the operation of the diffuser ("automatic diffuser stoppage"). This has the advantage of avoiding pointless operation of the diffuser and the inadvertent discharge of the battery if the driver has not himself turned off the diffuser.

In an alternate embodiment, the device schematised in FIG. 6 can also be integrated into the vehicle dashboard.

Figure 7:
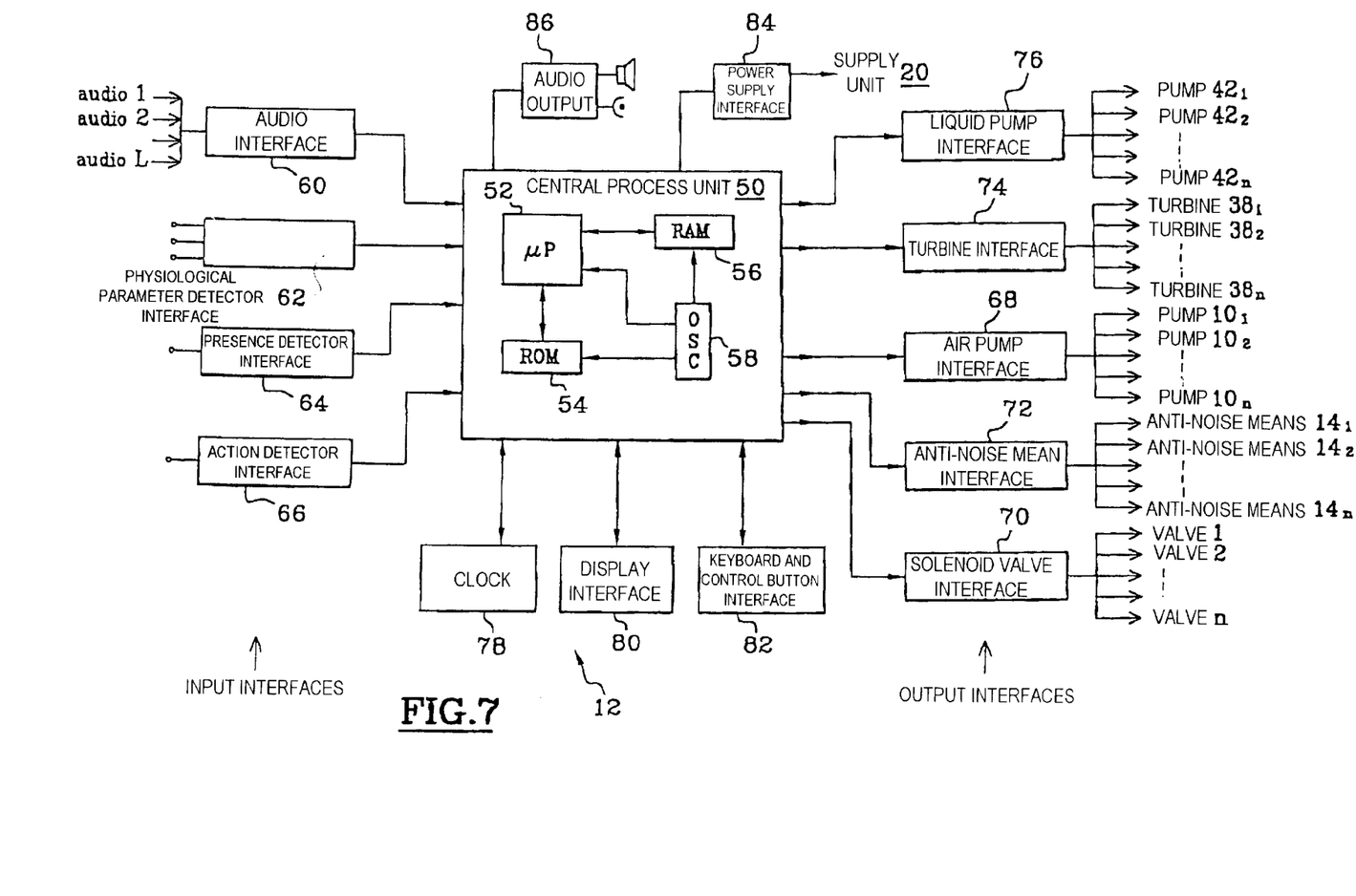
FIG. 7 is a schematic diagram of programmable control electronics designed to control the device in conformity with this invention.

FIG. 7 is a functional diagram of the main components of the control electronics 12 applicable in full or in part to each embodiment of the invention. In the example of FIG. 7, the control electronics 12 can be used with the five methods of embodiment described; accordingly, some of the interfaces depicted may only concern some of these embodiments.

The control electronics 12 is centred on a central processing unit 50 managing all of the programmable vaporisation devices of FIGS. 1 to 6.

The central processing unit 50 includes a microprocessor 52 programmed to perform a management execution programme from software recorded in read-only memory (ROM) 54. A random-access memory (RAM) 56 is connected to microprocessor 52 in order to change with it any evolutionary data, in particular parameter set-up and user programming data for the performance of various sequences to activate combinations of drop diffusion means 4.

All the components 52, 54, 56 are timed by an oscillator 58 which can also be used as a time base for the overall system.

The central processing unit 50 manages a set of interfaces associated with single inputs which may be internal or external with respect to the programmable vaporisation devices of FIGS. 1 to 6, i.e.:

an audio interface 60 for input connection of various audio sources (audio 1, audio 2, . . . audio L) which can be incorporated into the devices of FIGS. 1 to 6 or connected to them by wire or microwave links, such audio sources being, for instance: a compact disc player, a cassette player, one of several synthesised or recorded sound generators, etc;

a user physiological parameter detector interface 62 enabling the activation of various programmed functions, for instance: depending on the breathing rate (by detection of the dilation of the lung, breathing flux, breathing sound), snoring noises, the electrical activity of the nervous system (electroencephalogram or other means), etc, or physiological detectors that can be incorporated into the device 1 or connected to it;

a presence detector interface 64 designed to activate the various functions programmed according to a detected presence whereby the presence detector(s) can be incorporated into the device 1 or connected to it; and an action detector interface 66 designed to activate the various functions programmed according to a detected action, for instance, the opening of a door, the starting of an external device, the presence of background noises (the programmable vaporisation may then be sequences according to these sound), etc, whereby the presence detector(s) can be incorporated into the device 1 or connected to it.

The central processing unit 50 also manages the output interfaces enabling the operation of certain vaporisation production means 4 according to various production modes and according to production and according to the programming and the signals present at the various input interfaces. In the following, the elements of the programmable vaporisation devices of FIGS. 1 to 6 previously described separately are identified by the same reference number which is associated with a sub-index denoting the ranking in the multitude whereby device 1 here comprises n drop diffusion means 4, where n is greater than 1. These interfaces include:

an interface 68 controlling the turbines 10a of air pumps 101–10n used in particular for adjusting the flow of air to each second tube 261–26n when the device uses an individual pump for each drop diffusion means 4;

an interface 70 controlling the solenoid valves e. vannel,—e.vannen associated with outlets 10a1–10an of the air pump 10 when the device uses a single air pump 10;

an interface 72 on the anti-noise devices 141–14n according to the choices and methods used, the performing of calculations relative to the performing of the anti-noise function can be accomplished at least in part by the central processing unit 50;

an interface 74 for the fan(s) 381–38n, in particular for the control of the latter in the second embodiment; and an interface 76 of the liquid pumps 421–42n used for controlling the flow of liquid, and therefore the jet 46, in the third embodiment.

In terms of user interfaces, the central processing unit also manages the control interface 16, breaking down functionality and this level into three separate elements, i.e.:

a clock 78 used for executing the vaporisation programs (the directions, a mission intervals) depending on the time, a programmed interval or a down count);

an interface 80 controlling the display 1621 in order to present at the various operating and programming parameters; and a keyboard and control button interface 82 used for the input of various commands toward the central processing unit 50 for execution.

In addition, the central processing unit 50 controls through a power supply interface 84 the output of various voltages needed for the operation of the elements under control: diffusion means 4, interfaces, connected devices, etc.

Finally, the central processing unit 50 manages an audio output circuit 86, in particular to reproduce the signals supplied to the audio input interface 60 as a function of programmed parameters, audio production means (amplifier and speaker or earphone output) which can be incorporated into the programmable vaporisation device 1 or connected to it by a wire or microwave link.

In this way, the control electronics 12 by programming under the control of the central processing unit 50, can be used to define and choose at any time the emission combinations of a number p of diffusers among the n diffusers available where p is an integer that is less than or equal to n. In this way, within the volume emitted at a given moment, it is possible to obtain the mixture of p odours or active principles. The following moment, if necessary, it will be possible to choose p' out of the n available and so on where p' is an integer different from p and less than or equal to n. In other words, the number and/or combination of diffusion means 4 in the active state changes in the course of time, depending on programming managed by the device.

By choosing different combinations and successive moments of time, in this way, it is possible to construct variable sequences of odour combinations or of other active principles, etc.

The control electronics 12 can thus manage the n diffusion means 4, in association with a software programmed in the memory, structured around the time it takes to establish odour peak emission cycles having determined emission times and determined intervals between two successive emissions, as explained in the description. Control electronics 12 is capable of managing n diffusion means 4 by virtue of three user perception systems as a function of examples of use, i.e.:

- the sense of smell, whose capacities we are seeking to optimise,
- the state of being awake and asleep, generally associated with day and night, activity and rest, cerebral activity or its malfunctioning (coma) and,
- the sense of hearing, by associating sound sources with the operation of the means of diffusion 4.

The multiplicity of the means of diffusion 4 and the programming of combinations forming a varied sequences will provide access to various areas for the use of the devices contracted according to the invention, which will now be described by means of examples.

In these examples, the number n of diffusion outputs of different product is chosen according to the applications in view.

It will be understood that in the following examples, the described functions and cycles are obtained by programming managed at central processing unit 50 and the interfaces under control.

The multiplicity of diffusers 4 and the programming of combinations p, p', . . . forming varied sequences provide access to a variety of fields of use of programmed diffusion devices 1, as will appear in the non-limitative examples given below.

Application 1: Area of Practical Life

This particular application, linked with being awake and asleep, will be illustrated by the two following examples.

EXAMPLE 1

The diffusion devices used as and olfactory morning way Device and/or a means of accompaniment in falling asleep.

The device is designed to be placed near the user who chooses the time he wishes to wake up (for instance, accusing the programming unit 162 with the keyboard 82 and clock At this time, the diffusion device initiates the activation of the device generating the odour bearing product 78, (cf. FIG. 7) for instance, an essential oil, chosen for its activity and according to the preferences of the user. Diffusion will continue on its own for several tens of seconds and will be repeated after interruption kn times, thus generating odour peaks which, for some users, are sufficient to awaken them. If the user fails to wake up at this time, a noise is emitted by the device 1, by similar means, in order to awaken them. This noise can consist of natural sound, such as a waterfall, or the sound of crickets.

After several minutes, and therefore after several odour peaks, a mesmerised audio message, or a message reproduced in device 1 (or supplied externally by means of the audio interface 60, FIG. 7), consistently completes the olfactory message.

If, at this time, the user has already been awakened by the odour emitted by diffusion, the noises will nevertheless have an appeasing, character, easing the sleeper gently and agreeably out of his sleep.

Then, programming will turn off the sound after a few minutes while the cycle of projection of odour-bearing and/or essential oil (in this example) may be continued according to the control options programmed into the central processing unit 50.

Conversely, the same system can be used during the process of falling asleep, beginning by an association of noises, such as recorded or synthesised nature sounds and the projection of odour-bearing product (for instance, essential oils), then continuing with the emission of the odour-bearing product (essential oils) alone.

The devices of FIGS. 1 to 6 can also be programmed to detect the falling asleep at the user or an undesirable effect of this slumber, for instance, snoring.

For the process of falling asleep, it is possible, for instance, to measure the breathing rate so as to modify the sound level of the emitted sound effects and the emission of the odour-bearing product through to its stoppage. As far as snoring is concerned, the discreet emission of a suitable odour-bearing product will modify the breathing conditions and stop the snoring.

The detection of an operating condition permitting this cycle modification can be obtained by a suitable sensor connected to one of the input interfaces 60 to 66, depending on the control parameter. For instance, in the case of snoring being detected, a microphone near the snoring sleeper could be connected to audio interface 60 or possibly to the action detection interface 66, whereby the action in this case is an exceeding of the sound threshold detected by conventional electronics.

By the multiplicity of diffusion means 4 incorporated into the devices illustrated in FIGS. 1 to 6, it will be possible to offer a range of perfumes, for instance to emit and odour that smells less strongly in the case of falling asleep than in that of awakening.

Can be programmed means could be combined with other controlled means, for instance a more conventional alarm triggering a bell, tones, the radio, etc, included in device 1 or connected from the outside.

Application 2: Use of Device for Therapy

EXAMPLE 2

This example is based on more particular programming of the device 1 in conformity with this invention, with the intention of awakening a patient from a comatose state.

It is a well-known fact that the process of awakening from a comatose state often requires strong solicitations of the patient. The solicitations like this are often obtained by the presence and sound of loved ones.

This example of the implementing of the invention makes it possible to complete oral solicitations by olfactory solicitations. Preferably, it will be possible to choose odours having a relationship with the patient's past and an emission cycle will be programmed on device 1 by the practitioner or the operator through interfaces 80 and 82 (FIG. 7).

In this cycle implementation, the odours in question could even be pheromones relating to the affiliation of the patient or his affective life (spouse, children etc). For this purpose, a bank of pheromones could be stored to cater to the possibility of association with therapy at a later stage, in the same way as the a store of blood can be compiled by the patient himself, with a view to the performing of an operation on him. With means of preserving pheromones over long periods of time, the therapy could be implemented several years after the stock is compiled.

In these two examples, the functions of falling asleep and of waking up are all the more beneficial in that the apparatus does not interfere with the sleep of the user. The means described allowing the silent operation of the drop diffusion means are particularly advantageous: passive phonic installation, active anti-noise means 14, very low sound emission diffuser technology.

EXAMPLE 3

The device illustrated in FIGS. 1 to 6 is programmed in the central processing unit 50 to emit, according to a predetermined sequence or on the control of the user, drops to provide anti-smoking care. The emission of odour bearing product(s) and designed to be a smoking deterrent could be carried out at times of the day when the user suffers from the strongest smoking pangs.

Application 3: Implementation of Device 1 in the World of Play, Education or Scientific Research

EXAMPLE 4

The device illustrated in FIGS. 1 to 6 is programmed in the central processing unit 50 to diffuse a single odour or one odour at a time, through one of the n drop diffusion means 4, thus wide-ranging odours according to a programmed and timed sequence.

EXAMPLE 5

This example is similar to Example 3, but in this case, programming is designed for the diffusion of a combination of odour mixtures by two or three more than in more outlets, and even changing the pair or the group of three in the time-related sequence and so on. This combination of associations could be made more complex by programming the emission times and intervals for each of the n drop diffusion means 4 considered separately.

This programming of times and intervals, in particular, would make it possible to adapt to the time constant specific to the olfactory nerve endings and fibres of human beings (or possibly of animals for scientific research purposes). In particular, this could be a way of avoiding phenomena of the continuation or disappearance of the sense of smell by saturation or habituation: replacement of constant odours by "odour peaks". To do this, in particular, it would be possible to program the operation of the device according to the type of odour so that the emission duration, the intervals and the waiting durations strengthen the olfactory need and the desire to smell the chosen odour. In particular, this objective could be achieved in the device by recognition, for instance mechanical or electrical, of the type of cartridge and of the type of odour that the user has inserted into the device. This is a way of allowing for the fact that the impregnation times of nerve fibres, relaxation and waiting, vary according to the odour bearing substance used (for instance, essential oil) and where applicable, according to the individual.

In all of the described embodiments, the device can be equipped with means of automatically recognising the active product to be diffused. This recognition can be obtained more particularly by the encoding of the recipient (cartridge or other product container) which is legible by a reading arrangement on the device itself. Means like this could be based upon:

barcodes since a barcode label could be attached to the tank or cartridge 6 depending on its contents, and a barcode reader incorporated into the receptacle for the tank or cartridge;

mechanical means, for example, pins, hollows etc, on part of the tank or cartridge with a configuration specific to the product it contains and which configuration is detected by sensors incorporated into the receptacle for the tank or cartridge; or any other arrangement and an electronic chip supported by the cartridge were tank and containing condemning information specific to the product it contains which chip could be read by a communication interface incorporated into device 1.

It is understandable that the information given regarding the engineering methods and the applications envisaged may be combined depending on the desired results.

What is claimed is:

1. A programmable odor-bearing substance diffusion device comprising a number n of odor diffusion means, where n is equal to or greater than 1, each said odor diffusion means including a store of an odor source which is dispensed by the odor diffusion means, means for independently controlling each said odor diffusion means to emit a single odor or a mixture of odors from a combination of p of the n stores, and programmable control means for establishing odor peak emission cycles and a predetermined interval between two successive emission cycles, said predetermined interval being based on an olfactory saturation and desaturation times of the olfactory system of a user.

2. A device according to claim 1, wherein the odor peak emission cycles have an emission duration of five seconds to two minutes and the intervals between successive emission cycles is between two minutes and one hour.

3. A device according to claim 1, wherein the odor peaks have emission durations of fifteen seconds to one minute and intervals between emissions of between two minutes and five minutes.

4. A device according to claim 1, wherein the number n of odor diffusion means is equal to or greater than 2.

5. A device according to claim 1, additionally comprising active means for attenuation or elimination of noise in the form of anti-noise means.

6. A device according to claim 1, including passive noise attenuation means.

7. A device according to claim 1, wherein the diffusion means includes means constructed and arranged to emit droplets sized so as to produce a dry fog effect, where the elementary diameter of said droplets is in the region of 0.5 to 3 microns.

8. A device according to claim 1, wherein the diffusion means operates by Venturi effect.

9. A device according to claim 1, wherein the diffusion means includes an electromechanical actuator constructed and arranged to transmit vibrations to a load of liquid contained in a cavity so as to eject the droplets of the liquid load.

10. A device according to claim 1, wherein the diffusion means includes means for production of a liquid jet to be diffused and means for generating surface acoustic waves on the liquid jet so as to detach the droplets from the jet.

11. A device according to claim 1, wherein the diffusion means comprises means for surface evaporation.

12. A device according to claim 1, wherein the programmable control means includes means for signal input constructed and arranged to be connected to at least one physiological parameter sensor capable of controlling an odor diffusion program as a function of at least one detected physiological parameter.

13. A device according to claim 12, associated with a physiological parameter sensor comprising a detector for detecting noise caused by snoring, the device being programmed to control the diffusion means so as to emit an odor-bearing product in response to detected snoring so as to cause it to cease.

14. A device according to claim 1, associated with a drowsiness state physiological parameter sensor, said device being programmed to control the diffusion means and cause the emission of the product as a function of a detected physiological state.

15. A device according to claim 13, wherein the physiological sensor includes at least one detector selected from the group consisting of a breathing detector and a detector of characteristic electrical state of the user.

16. A device according to claim 1, wherein the programmable means of control comprises time counting means so as to control an odor diffusion program depending on at least one time-related parameter.

17. A device according to claim 1, wherein the programmable control means is programmed so as to begin, at a programmed time, an odor diffusion cycle capable of causing a subject to awaken.

18. A device according to claim 1, wherein the programmable control means is programmed so as to begin, at a programmed time or in response to an input at an interface thereof, an odor diffusion cycle suitable to accompany a subject falling asleep.

19. A device according to claim 1, wherein the programmable control means includes audio means capable of controlling the emission of sounds to accompany an odor emission program.

20. A device according to claim 1, wherein the odor diffusion means comprises at least one tank containing an odor-bearing liquid specific to that tank.

21. A device according to claim 1, constructed and arranged for soliciting awakening of a patient from a comatose state, and comprising at least one tank containing an odor-bearing liquid chosen to emit an odor related to the past or surroundings or tastes of a patient.

22. A device according to claim 21, wherein at least one of odors is based on a pheromone related to the filiation of affective life of the patient.

23. A device according to claim 1, wherein the odor peak generation cycles are calculated taking into consideration a saturation and desaturation time of the olfactory nerve system and adding to it a latent time likely to give a user the desire to create it so as to hasten the process and renew his pleasure when the odor peak arrives.

24. A device according to claim 1, including automatic means of recognition of the product by virtue of a predetermined encoding facility forming the store and adjusting the diffusion program accordingly.

25. A device according to claim 1, further comprising an electric power supply adapted for connection to an electric circuit of a vehicle.

26. A device according to claim 1, which is a portable unit allowing personal and individual use.

27. A device according to claim 1, including audio means associated with the odor diffusion means for sending a consistent odor-sound message related to nature.

* * * * *